United States Patent
Suzuki et al.

(10) Patent No.: US 9,850,511 B2
(45) Date of Patent: Dec. 26, 2017

(54) BIOMASS PROCESSING SYSTEM AND SACCHARIDE-SOLUTION PRODUCTION METHOD USING BIOMASS MATERIAL

(75) Inventors: Hideo Suzuki, Tokyo (JP); Yoshio Kuromi, Tokyo (JP); Yoshitaka Kimura, Tokyo (JP)

(73) Assignee: MITSUBISHI HITACHI POWER SYSTEMS ENVIRONMENTAL SOLUTIONS, LTD., Yokohama-shi (JP)

( * ) Notice: Subject to any disclaimer, the term of this patent is extended or adjusted under 35 U.S.C. 154(b) by 384 days.

(21) Appl. No.: 13/203,929

(22) PCT Filed: Jul. 9, 2010

(86) PCT No.: PCT/JP2010/061725
§ 371 (c)(1),
(2), (4) Date: Aug. 30, 2011

(87) PCT Pub. No.: WO2012/004895
PCT Pub. Date: Jan. 12, 2012

(65) Prior Publication Data
US 2012/0009626 A1    Jan. 12, 2012

(51) Int. Cl.
| | | |
|---|---|---|
| C12P 19/02 | (2006.01) | |
| C12M 1/40 | (2006.01) | |
| C12M 1/33 | (2006.01) | |
| C12P 7/10 | (2006.01) | |
| C12P 19/14 | (2006.01) | |
| D21C 1/04 | (2006.01) | |
| C12M 1/00 | (2006.01) | |

(52) U.S. Cl.
CPC ............. *C12P 19/02* (2013.01); *C12M 21/12* (2013.01); *C12M 21/18* (2013.01); *C12M 45/02* (2013.01); *C12M 45/04* (2013.01); *C12M 45/09* (2013.01); *C12M 45/20* (2013.01); *C12P 7/10* (2013.01); *C12P 19/14* (2013.01); *D21C 1/04* (2013.01); *C12M 47/00* (2013.01); *C12P 2201/00* (2013.01); *Y02E 50/16* (2013.01)

(58) Field of Classification Search
None
See application file for complete search history.

(56) References Cited

U.S. PATENT DOCUMENTS

| | | |
|---|---|---|
| 3,985,728 A | 10/1976 | Lin |
| 4,023,982 A | 5/1977 | Knauth |
| 4,152,197 A | 5/1979 | Lindahl et al. |
| 4,384,897 A | 5/1983 | Brink |
| 4,650,689 A | 3/1987 | Hedrick |
| 4,746,401 A | 5/1988 | Roberts et al. |
| 4,822,737 A | 4/1989 | Saida |
| 4,859,322 A | 8/1989 | Huber |
| 5,348,871 A * | 9/1994 | Scott et al. ................. 435/165 |
| 5,411,594 A | 5/1995 | Brelsford |
| 5,424,417 A | 6/1995 | Torget et al. |
| 5,466,108 A | 11/1995 | Piroska |
| 6,022,419 A | 2/2000 | Torget et al. |
| 6,419,788 B1 | 7/2002 | Wingerson |
| 8,123,864 B2 | 2/2012 | Christensen et al. |
| 8,163,517 B2 | 4/2012 | Genta et al. |
| 8,728,770 B2 | 5/2014 | Ishikawa et al. |
| 9,102,956 B2 | 8/2015 | Genta et al. |
| 2007/0231869 A1 | 10/2007 | Holmgren et al. |
| 2007/0259412 A1 | 11/2007 | Belanger et al. |
| 2008/0026431 A1 | 1/2008 | Saito et al. |
| 2008/0032344 A1 | 2/2008 | Fallavollita |
| 2008/0044891 A1 | 2/2008 | Kinley et al. |
| 2010/0041119 A1 | 2/2010 | Christensen et al. |
| 2010/0108567 A1 | 5/2010 | Medoff |
| 2010/0184176 A1 | 7/2010 | Ishida et al. |
| 2010/0269990 A1 | 10/2010 | Dottori et al. |
| 2010/0285574 A1 | 11/2010 | Genta et al. |
| 2010/0317843 A1 | 12/2010 | Sudhakaran et al. |
| 2010/0330638 A1 | 12/2010 | Aita et al. |

(Continued)

FOREIGN PATENT DOCUMENTS

| | | |
|---|---|---|
| CA | 2660990 A1 | 8/2009 |
| CA | 2666152 A1 | 4/2010 |

(Continued)

OTHER PUBLICATIONS

Gregg et al. "Bioconversion of Lignocellulosic Residue to Ethanol: Process Flowsheet Development" Biomass and Bioenergy, vol. 9, Nos. I-5. pp. 287-302, 1995.*
U.S. Office Action dated Nov. 4, 2013, issued in U.S. Appl. No. 13/203,848.
U.S. Office Action dated Aug. 19, 2013, issued in U.S. Appl. No. 13/578,116.
U.S. Office Action dated Oct. 3, 2013, issued in U.S. Appl. No. 13/782,545.
Arroyo-Lopez, F.N. et al., "Effects of temperature, pH and sugar concentration on the growth parameters of *Saccharomyces cerevisiae*, S. kudriavzevii and their interspecific hybrid", International Journal of Food Microbiology, vol. 131, pp. 120-127 (2009).

(Continued)

*Primary Examiner* — Thane Underdahl
(74) *Attorney, Agent, or Firm* — Westerman, Hattori, Daniels & Adrian, LLP

(57) ABSTRACT

A hydrothermal decomposition apparatus 17 as a biomass processing apparatus that decomposes a biomass material 11 into cellulose, hemicellulose, and lignin under a high temperature and high pressure condition to remove a lignin component and a hemicellulose component, a biomass solid discharging unit 18 that discharges a biomass solid (a hot-water insoluble component) 20 processed in the hydrothermal decomposition apparatus 17, and a slurrying vessel 21 communicating with the biomass solid discharging unit 18, into which water 19 is injected and the discharged biomass solid 20 is added to make it slurried are provided to an apparatus body 13, which is a processing vessel having a gas-liquid interface 13*a*.

3 Claims, 10 Drawing Sheets

(56) References Cited

U.S. PATENT DOCUMENTS

| | | |
|---|---|---|
| 2011/0003348 A1 | 1/2011 | Genta et al. |
| 2011/0079219 A1 | 4/2011 | McDonald et al. |
| 2011/0314726 A1 | 12/2011 | Jameel et al. |
| 2012/0006320 A1 | 1/2012 | Nguyen |
| 2012/0009642 A1 | 1/2012 | Suzuki et al. |
| 2012/0315683 A1 | 12/2012 | Mosier et al. |
| 2013/0122555 A1 | 5/2013 | Suzuki et al. |
| 2014/0004571 A1 | 1/2014 | Garrett et al. |
| 2014/0273127 A1 | 9/2014 | Fuchs et al. |

FOREIGN PATENT DOCUMENTS

| | | |
|---|---|---|
| CA | 2 750 754 A1 | 1/2012 |
| CA | 2654306 C | 10/2013 |
| EP | 0 098 490 A2 | 1/1984 |
| JP | 9-507386 A | 7/1997 |
| JP | 11-506934 A | 6/1999 |
| JP | 2001170601 A | 6/2001 |
| JP | 2002-059118 A | 2/2002 |
| JP | 2003-311141 A | 11/2003 |
| JP | 2004-105855 A | 4/2004 |
| JP | 2005-27541 A | 2/2005 |
| JP | 2005-168335 A | 6/2005 |
| JP | 2005-205252 A | 8/2005 |
| JP | 2005-229821 A | 9/2005 |
| JP | 2006-036977 A | 2/2006 |
| JP | 2006-136263 A | 6/2006 |
| JP | 2006-223152 A | 8/2006 |
| JP | 2006-289164 A | 10/2006 |
| JP | 2007112880 A | 5/2007 |
| JP | 2007-202560 A | 8/2007 |
| JP | 2007-301472 A | 11/2007 |
| JP | 2008-054608 A | 3/2008 |
| JP | 2008-104452 A | 5/2008 |
| JP | 2008-278825 A | 11/2008 |
| JP | 2009-183153 A | 8/2009 |
| JP | 2009-183154 A | 8/2009 |
| JP | 2009-183805 A | 8/2009 |
| JP | 2010-17084 A | 1/2010 |
| JP | 4436429 B1 | 3/2010 |
| JP | 4764527 B1 | 9/2011 |
| JP | 4764528 B1 | 9/2011 |
| WO | 84/003304 A1 | 8/1984 |
| WO | 95/17517 A1 | 6/1995 |
| WO | 96/40970 A1 | 12/1996 |
| WO | 2009/096060 A1 | 8/2009 |
| WO | 2009/096061 A1 | 8/2009 |
| WO | 2009/096062 A1 | 8/2009 |
| WO | 2009/124240 A1 | 10/2009 |
| WO | 10/038302 A1 | 4/2010 |
| WO | 2013/082616 A2 | 6/2013 |
| WO | 2013/083616 A2 | 6/2013 |

OTHER PUBLICATIONS

Turton, L.J. et al., "Effect of Glucose Concentration in the Growth Medium Upon Neutral and Acidic Fermentation End-products of Clostridium Bifermentans, Clostridium Sporogenes and Peptostreptococcus Anaerobius", J. Med. Microbiol., vol. 16, pp. 61-67 (1983).

Dien, B.S. et al., "Fermentation of hexose and pentose sugars using a novel ethanologenic *Escherichia coli* strain", Enzyme and Microbial Technology, vol. 23, pp. 366-371 (1998).

International Search Report of PCT/JP2010/061724, dated Oct. 5, 2012.

Written Opinion of PCT/JP/2010/061724.

U.S. Office Action dated Apr. 23, 2013, issued in copending U.S. Appl. No. 13/203,848.

Machine Translation of JP 2006-136263, in U.S. Office Action dated Apr. 23, 2013.

Nikkei Biotechnology & Business, Sep. 2002, pp. 52-61.

International Search Report of PCT/JP2010/061725, dated Oct. 12, 2010.

Written Opinion of PCT/JP2010/061725, dated Oct. 12, 2010.

Canadian Notice of Allowance dated Aug. 22, 2013, issued in Canadian Patent Application No. 2666152.

Canadian Notice of Allowance dated Aug. 22, 2013, issued in Canadian Patent Application No. 2713529.

U.S. Office Action dated Oct. 28, 2013, issued in U.S. Appl. No. 12/443,515.

U.S. Office Action dated Oct. 7, 2013, issued in U.S. Appl. No. 13/700,753.

Kumagai Satoshi et al. "Fractionation and Saccharification of Cellulose and Hemicellulose in Rice Hull by Hot-Compressed-Water Treatment with Two-Step Heating", Journal of the Japan Institute of Energy, Dec. 1, 2003 (Dec. 1, 2003), vol. 83, pp. 776-781, Cited in Notice of Acceptance dated Mar. 4, 2014, issued in Japanese Patent Application No. 2009-252201.

U.S. Final Office Action dated Feb. 13, 2014, issued in U.S. Appl. No. 12/865,273 (26 pages).

Liu, Chaogang, et al., "Continuous Fermentation of Hemicellulose Sugars and Cellulose to Ethanol", International Symposia on Alcohol Fuels, (2005), pp. 1-28 (cited in U.S. Final Office Action dated Feb. 13, 2014, issued in U.S. Appl. No. 12/865,273.

U.S. Non-Final Office Action dated Mar. 10, 2014, in U.S. Appl. No. 13/782,545 (27 pages).

Decision of a Patent Grant dated Mar. 4, 2014, issued in JP2009-252201 (corresponding to U.S. Appl. No. 12/443,515), w/English translation (4 pages).

Decision of a Patent Grant dated Mar. 4, 2014, issued in JP2009-245963 (corresponding to U.S. Appl. No. 12/438,792) w/English translation (4 pages).

Australian Notice of Acceptance dated Mar. 17, 2014, issued in Australian patent application No. 2011355013 (corresponding to U.S. Appl. No. 13/578,116) (2 pages).

U.S. Office Action dated Apr. 14, 2014, issued in U.S. Appl. No. 12/443,515 (16 pages).

Canadian Office Action dated Nov. 8, 2013, issued in Canadian Patent Application No. 2,801,383 (2 pages).

Indonesian Notice of Allowance dated Nov. 15, 2013, issued in Indonesian Patent Application No. W-00201002623, w/English translation, (5 pages).

Canadian Notice of Allowance dated Jan. 13, 2014, issued in Canadian Patent Application No. 2,744,522 (1 page).

U.S. Non-Final Office Action dated Dec. 16, 2013, issued in U.S. Appl. No. 13/132,034 (29 pages).

U.S. Non-Final Office Action dated Jan. 30, 2014 issued in U.S. Appl. No. 12/438,792 (39 pages).

U.S. Non-Final Office Action dated Jan. 30, 2014, issued in U.S. Appl. No. 13/578,116 (22 pages).

Decision of a Patent Grant dated Nov. 12, 2013, issued in Japanese Patent Application No. 2013-536355, w/ English translation (corresponds to U.S. Appl. No. 14/381,511) (4 pages).

U.S. Office Action dated Apr. 24, 2015, issued in U.S. Appl. No. 14/381,511 (20 pages).

Notice of Allowance and Fee(s) Due dated Feb. 17, 2015, issued in U.S. Appl. No. 13/782,545 (20 pages).

U.S. Office Action dated Mar. 19, 2015, issued in U.S. Appl. No. 13/121,969 (21 pages).

U.S. Office Action dated Mar. 13, 2015, issued in U.S. Appl. No. 13/722,385 (41 pages).

Notice of Allowance and Fee(s) Due dated Apr. 2, 2015, issued in U.S. Appl. No. 13/132,040 (17 pages).

U.S. Office Action dated Mar. 31, 2015, issued in U.S. Appl. No. 12/865,273 (25 pages).

U.S. Office Action dated May 13, 2015, issued in U.S. Appl. No. 12/438,792 (11 pages).

U.S. Final Office Action dated Jul. 3, 2014, issued in U.S. Appl. No. 13/578,116 (17 pages).

U.S. Final Office Action dated Aug. 18, 2014, issued in U.S. Appl. No. 13/132,034 (30 pages).

U.S. Final Office Action dated Jun. 13, 2014, issued in U.S. Appl. No. 12/438,792 (26 pages).

U.S. Non-Final Office Action dated Aug. 27, 2014, issued in U.S. Appl. No. 13/132,040 (53 pages).

(56) References Cited

OTHER PUBLICATIONS

U.S. Final Office Action dated Jul. 22, 2014, issued in U.S. Appl. No. 12/443,515 (13 pages).
Office Action dated Sep. 25, 2015 issued in co-pending U.S. Appl. No. 13/132,034 (39 pages).
Office Action dated Sep. 28, 2015 issued in co-pending U.S. Appl. No. 13/1203,848 (34 pages).
Office Action dated Jul. 10, 2015 issued in Australian application No. AU2012374915, counterpart to U.S. Appl. No. 13/132,034 (in English) (5 pages).
Notice of allowance dated Sep. 30, 2015 issued in Canadian application No. 2,791,665, counterpart to U.S. Appl. No. 13/132,034 (in English) (1 page).
Decision of a Patent Grant dated Nov. 10, 2015, issued in Japanese patent application No. 2010-154233, counterpart to co-pending U.S. Appl. No. 13/700,753 (w/ English translation, 5 pages).
Canadian Office Action dated Mar. 31, 2014, issued in Canadian Patent Application No. 2,750,753 (3 pages) (corresponding to U.S. Appl. No. 13/203,929).
U.S. Final Office Action dated May 22, 2014, issued in U.S. Appl. No. 13/700,753 (40 pages).
Indonesian Office Action dated Nov. 7, 2014, issued in IDW-00200902414, w/English translation (corresponds to U.S. Appl. No. 12/438,792) (6 pages).
Indonesian Office Action dated Nov. 14, 2014, issued in IDW-00201102352, w/English translation (corresponds to U.S. Appl. No. 13/121,969) (7 pages).
Lehrburger, E. "Developing biorefineries to produce energy, ethanol and other industrial products", PureVision Technology, Inc., Alternative Energy Conference, Mar. 3, 2005, pp. 1-26, Cited in U.S. Office Action dated Nov. 6, 2014.
U.S. Office Action dated Sep. 30, 2014, issued in U.S. Appl. No. 13/782,545 (43 pages).
U.S. Office Action dated Nov. 6, 2014, issued in U.S. Appl. No. 12/865,273 (27 pages).
Japanese Office Action dated Oct. 14, 2014, issued in Japanese Patent Application No. 2010-154233 (corresponding to U.S. Appl. No. 13/700,753), with English Translation (7 pages).
Non-Final Office Action dated Jun. 19, 2015, issued in U.S. Appl. No. 13/700,753 (34 pages).
Final Office Action dated Aug. 6, 2015, issued in U.S. Appl. No. 14/381,511 (14 pages).
Notice of Allowance dated Aug. 19, 2015, issued in U.S. Appl. No. 12/438,792 (12 pages).
Notice of Allowance dated Aug. 12, 2015, issued in U.S. Appl. No. 13/578,116 (48 pages).
Notice of Allowance dated Jul. 6, 2015, issued in counterpart Indonesian application No. W-00201103522 (4 pages), with English translation.
Notice of Allowance dated Dec. 21, 2015, issued in co-pending U.S. Appl. No. 14/381,511 (11 pages) (including PTO892 and returned SB08).
Supplemental Notice of Allowability dated Jan. 8, 2016, issued in co-pending U.S. Appl. No. 14/381,511 (6 pages) (including returned SB08).
Notice of Allowance dated Feb. 3, 2016, issued in co-pending U.S. Appl. No. 13/578,116 (17 pages) (including returned SB08).
Notice of Allowance dated Mar. 14, 2016, issued in co-pending U.S. Appl. No. 13/121,969 (12 pages) (including return SB08).
Notice of Acceptance dated Mar. 16, 2016, issued in Australian Application No. 2012374915, counterpart to U.S. Appl. No. 14/381,511 (in English; 2 pages).
Notification of Allowance dated Mar. 30, 2016, issued in Indonesian Patent Application No. W-00200902414 (w/ English translation; 4 pages).
Office Action dated Apr. 22, 2016, issued in co-pending U.S. Appl. No. 13/132,034 (31 pages) (including returned SB08).
Office Action dated Apr. 18, 2016, issued in co-pending U.S. Appl. No. 13/722,385 (31 pages) (including returned SB08).
Notice of Allowance dated May 5, 2016, issued in co-pending U.S. Appl. No. 13/203,848 (23 pages) (including returned SB08).
International Search Report dated Jul. 3, 2012 issued in International Application No. PCT/JP2012/058460, counterpart to U.S. Appl. No. 14/381,511 (in English; 2 pages) (previously submitted in the IDS of May 15, 2015; resubmitted to provide page number).
Written Opinion of the International Searching Authority dated Jul. 3, 2012 issued in International Application No. PCT/JP2012/058460, counterpart to U.S. Appl. No. 14/381,511 (w/ English translation; 7 pages) (previously submitted in the IDS of May 15, 2015; resubmitted to provide page number).
Genda, M. et al., "Suinetsu Bunkaiho to Koso Bunkaiho o Kumiawaseta Nogyo Zansa to no Cellulose Biomass no Tei Cost Toka Gijutsu no Kaihatsu", Heisei 21 Nendo Biomass Energy Kanren Jigyo Seika Hokokukai, Feb. 11, 2010, pp. 55-69, URL, http://www.nedo.go.jp/events/report/FF_00003.html, cited in Japanese Office Action dated Oct. 14, 2014 (previously submitted in the IDS of Dec. 30, 2014; resubmitted with the citing Japanese Office Action).
Office Action dated Oct. 14, 2014, issued in Japanese Patent Application No. 2010-154233, counterpart to U.S. Appl. No. 13/700,753 (w/ English translation; 7 pages) (previously submitted in the IDS of Dec. 30, 2014; resubmitted with Genda, M. et al. cited therein).
Office Action dated Dec. 5, 2014, issued in co-pending U.S. Appl. No. 13/121,969 (31 pages) (including returned SB08) (previously submitted in the IDS of Dec. 30, 2014; resubmitted to provide page number).
Notice of Allowance dated Dec. 5, 2014, issued in Canadian Patent Application No. 2750754, counterpart to co-pending U.S. Appl. No. 13/203,848 (in English; 1 page) (previously submitted in the IDS of Dec. 30, 2014; resubmitted to provide page number).
Office Action dated Oct. 29, 2014, issued in Indonesian Patent Application No. W00201103522 (w/ English translation; 6 pages) (previously submitted in the IDS of Dec. 30, 2014; resubmitted to provide page number).
Notice of Allowance dated Nov. 5, 2014, issued in U.S. Appl. No. 12/443,515 (19 pages) (including returned SB08) (previously submitted in the IDS of Dec. 30, 2014; resubmitted to provide page number).
Office Action dated Dec. 26, 2014, issued in U.S. Appl. No. 13/132,040 (19 pages) (including returned SB08) (previously submitted in the IDS of Dec. 30, 2014; resubmitted to provide page number).
Notification of Result of Substantive Examination dated Mar. 30, 2016, issued in Indonesian Patent Application No. W-00201102351 (w/ English translation; 4 pages).
Notification of Allowance dated Aug. 8, 2016, issued in Indonesian Patent Application No. W-00201102351 (w/ English translation; 4 pages).
Notice of Allowance dated Oct. 5, 2016 in co-pending U.S. Appl. No. 13/722,385 (w/ returned PTO/SB/08a forms; 22 pages).
Office Action dated Sep. 29, 2016, issued in co-pending U.S. Appl. No. 14/411,473 (English; 33 pages; w/ PTO-892 and returned PTO/SB/08 forms).

\* cited by examiner

FIG.10
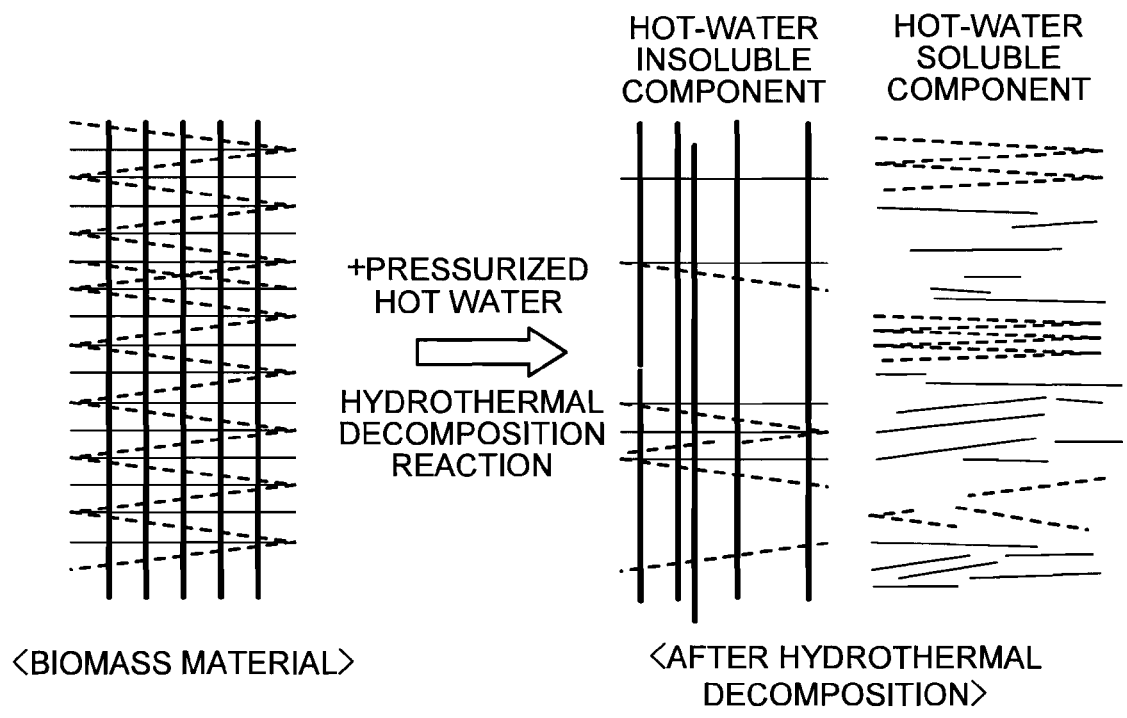
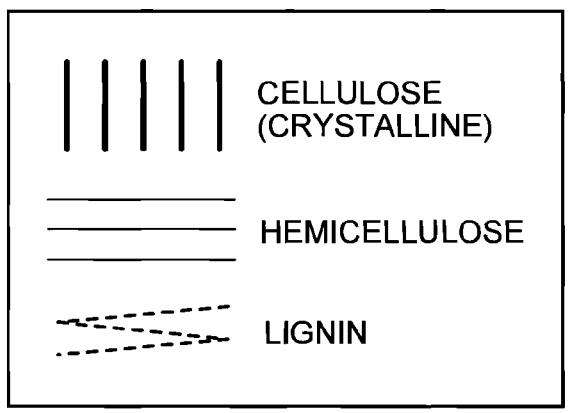

BIOMASS PROCESSING SYSTEM AND SACCHARIDE-SOLUTION PRODUCTION METHOD USING BIOMASS MATERIAL

FIELD

The present invention relates to a biomass processing system that can efficiently decompose a biomass material, a saccharide-solution production method using a biomass material, and an alcohol production method.

BACKGROUND

Conventionally, a technique for producing ethanol or the like, in which solid-liquid separation is performed after saccharification of biomass such as wood by using diluted sulfuric acid or concentrated sulfuric acid, and a liquid phase is neutralized and used as a raw material for ethanol fermentation, has been practically utilized (Patent Literature 1, Patent Literature 2).

Further, production of chemical industrial raw materials (for example, lactic acid fermentation) using saccharide as a starting material can also be considered.

In this specification, "biomass" represents organisms incorporated in a substance circulatory system of the global biosphere or accumulation of organic matters derived from the organisms (see JIS K 3600 1258).

Sugarcane, corn and the like, which are currently used as alcohol raw materials, are originally used as food and using these edible resources as industrial resources in a long term and in a stable manner is not preferable in view of a life cycle of effective foodstuff.

Therefore, it is an important issue to effectively use cellulose resources such as herbaceous biomass and woody biomass, which are believed to be useful industrial recourses in the future.

Further, in the cellulose resources, the resource component ratio is varied such that the ratio of cellulose is 38% to 50%, that of hemicellulose component is 23% to 32%, and that of lignin component, which is not used as a fermentation raw material, is 15% to 22%. Because industrial researches have been conducted with many unsolved problems, raw materials in the researches are assumed in a fixed manner, and currently there is no disclosure of a technique of a production system with taking the material versatility into consideration.

Originally, because issues of waste and prevention of the global warming are taken into consideration according to a method unfavorable to fermentation feedstock as compared with starch feedstock, there is less point in the production system in which raw materials are considered in a fixed manner. This production system should be widely applicable to general waste materials. Enzymatic saccharification method itself is not efficient at all, and is thought to be a challenge of the future. A saccharification rate by acid treatment has a considerably small value of about 75% (on a component basis capable of being saccharified) due to excessive decomposition of saccharide caused by overreaction. Therefore, the production yield of ethanol is about 25% with respect to the cellulose resources (Non Patent Literature 1, Patent Literature 3).

In the conventional techniques disclosed in Patent Literatures 1 to 3, there has been a phenomenon in which a reaction by-product causes inhibition of enzymatic saccharification to decrease the saccharide yield. Therefore, a hydrothermal decomposition apparatus that removes a substance inhibiting enzymatic saccharification to increase activity of enzyme based on cellulose has been proposed (Patent Literatures 4 and 5).

CITATION LIST

Patent Literatures

Patent Literature 1: Japanese Patent Application National Publication No. H9-507386
Patent Literature 2: Japanese Patent Application National Publication No. H11-506934
Patent Literature 3: Japanese Patent Application Laid-open No. 2005-168335
Patent Literature 4: Japanese Patent Application Laid-open No. 2009-183805
Patent Literature 5: Japanese Patent Application Laid-open No. 2009-183154

Non Patent Literature

Non Patent Literature 1: Nikkei Bio Business, p. 52, September 2002

SUMMARY

Technical Problem

In the hydrothermal decomposition apparatuses proposed in Patent Literatures 4 and 5 mentioned above, since the internal temperature is high, which is 180 to 240° C., and a pressure higher by 0.1 to 0.4 MPa is applied to a saturated vapor of water at respective temperatures, when discharging a biomass solid as it is from under an increased pressure to put it under a normal pressure after the reaction, there is a problem that the effluence of nitrogen, for example, which is a pressurized gas, occurs.

Further, a hydrothermal decomposition product discharged from a gas-liquid interface between the pressurized hot water and the pressurized gas in the hydrothermal decomposition apparatus is in a high temperature and high pressure state. As a result, the reaction is promoted, and there is a problem that the excessive decomposition of hot-water dissolved hemicellulose obtained after being dissolved in the hot water accompanying the biomass solid or hot-water insoluble cellulose occurs in a high temperature (180 to 240° C.) range. Not only in the hydrothermal decomposition but also in alkali treatment decomposition or acid treatment decomposition performing decomposition under a high temperature and high pressure state by means of the addition of alkali or acid, a similar phenomenon occurs.

Since the excessive decomposition of hemicellulose or cellulose as described above reduces a percentage of the raw material for a saccharide solution, it is desired to suppress such excessive decomposition so as to improve a plant operating efficiency.

In view of the above problems, the present invention provides a biomass processing system that can prevent the effluence of a pressurized gas when a biomass solid is discharged after a biomass material is decomposed under a high temperature and high pressure state and can suppress the excessive decomposition of cellulose or hemicellulose in the biomass material to efficiently obtain a valuable product. The present invention also provides a saccharide-solution production method using a biomass material, and an alcohol production method.

Means for Solving Problems

According to an aspect of the present invention, a biomass processing system includes: a biomass processing unit that decomposes a biomass material containing cellulose, hemicellulose, and lignin under a high temperature and high pressure condition by a processing vessel having a gas-liquid interface to remove a lignin component and a hemicellulose component; a biomass solid discharging unit that discharges a biomass solid processed in the biomass processing unit; and a slurrying vessel communicating with the biomass solid discharging unit, into which water is injected and the discharged biomass solid is slurried.

Advantageously, in the biomass processing system, the biomass processing unit is any one of a hydrothermal decomposition processing unit, an alkaline decomposition processing unit, and an acid decomposition processing unit.

Advantageously, the biomass processing system further includes a first solid-liquid separation device provided on a downstream of the slurrying vessel for removing water from the slurried biomass solid.

Advantageously, the biomass processing system further includes a first return line for recycling the water separated by the first solid-liquid separation device to the slurrying vessel.

Advantageously, the biomass processing system further includes a biological treatment vessel provided in the first return line, for performing biological treatment on the water separated by the first solid-liquid separation device. The biologically-treated water is returned to the slurrying vessel.

Advantageously, the biomass processing system further includes a first saccharification tank for saccharifying a biomass solid separated by the first solid-liquid separation device.

Advantageously, the biomass processing system further includes an enzyme liquefaction tank for performing enzyme liquefaction by adding an enzyme to the biomass solid separated by the first solid-liquid separation device. An enzyme liquefied product is saccharified by the enzyme in the first saccharification tank.

Advantageously, the biomass processing system further includes a second saccharification tank for saccharifying the slurried biomass solid slurried in the slurrying vessel.

Advantageously, the biomass processing system further includes: a solid-liquid separation device that separates a solid content from a saccharide solution after the saccharification; and a water separation device that removes water from a saccharide solution after the solid separation.

Advantageously, the biomass processing system further includes a second return line for recycling the water separated by the water separation device to the slurrying vessel.

Advantageously, the biomass processing system further includes a biological treatment device provided in the second return line.

According to another aspect of the present invention, a saccharide-solution production method using a biomass material includes: feeding a biomass material containing cellulose, hemicellulose, and lignin under a normal pressure to put it under an increased pressure, and decomposing the biomass material by a biomass processing unit under a high temperature and high pressure condition; thereafter, adding a biomass solid discharged from the biomass processing unit to a slurrying vessel containing water injected therein and communicating with the biomass processing unit so as to obtain a slurried biomass solid; then removing water from the slurried biomass solid; and thereafter, performing enzymatic saccharification of the biomass solid from which the water has been removed to produce a saccharide solution.

Advantageously, in the saccharide-solution production method using a biomass material, on an upstream of the enzymatic saccharification of the biomass solid from which the water has been removed, enzyme liquefaction of the biomass solid is performed.

According to still another aspect of the present invention, a saccharide-solution production method using a biomass material includes: feeding a biomass material containing cellulose, hemicellulose, and lignin under a normal pressure to put it under an increased pressure, and thermally decomposing the biomass material by a biomass processing unit; thereafter, adding a biomass solid discharged from the biomass processing unit to a slurrying vessel containing water injected therein and communicating with the biomass processing unit so as to obtain a slurried biomass solid; and performing enzymatic saccharification of the slurried biomass solid to obtain a saccharide solution, thereafter, separating a solid content therefrom, and then removing water therefrom.

According to still another aspect of the present invention, in an alcohol production method, alcohol fermentation is performed using the saccharide solution obtained by the saccharide-solution production method using a biomass material according to any one of above method so as to produce alcohol.

Advantageous Effects of Invention

According to the present invention, by adding the processed biomass solid into the liquid in the slurrying vessel containing water injected therein, the biomass solid is slurried and liquid seal is achieved. As a result, it is possible to prevent the effluence of the pressurized gas. Thus, the effluence of a pressurizing gas (for example, pressurized nitrogen or the like) is prevented, thereby achieving a reduction in the running cost.

Further, since the biomass solid is added into the liquid, the biomass solid is cooled by the direct heat exchange with the liquid. Therefore, the reaction can be efficiently terminated. Also, since acid or alkali is diluted, the excessive decomposition of residual hemicellulose, residual lignin, and the main component, cellulose, accompanying the biomass solid is suppressed. As a result, the generation of the reaction inhibiting component can be suppressed, and the recovery rate of the cellulose component can be improved.

BRIEF DESCRIPTION OF DRAWINGS

FIG. 10 is a diagram showing how biomass is decomposed by hot water.

DESCRIPTION OF EMBODIMENTS

The present invention will be described below in detail with reference to the drawings. The present invention is not limited by the embodiments. In addition, constituent elements in the following embodiments include those that can be easily assumed by persons skilled in the art or that are substantially equivalent. While a hydrothermal decomposition apparatus is used as a biomass processing unit that processes a biomass material in the embodiments, the present invention is not limited to this device. A similar operation can be applied also in a system for decomposing a biomass material by the addition of acid or alkali.

First Embodiment

The biomass processing system according to the present invention will be described with reference to the drawings.

Figure 1:
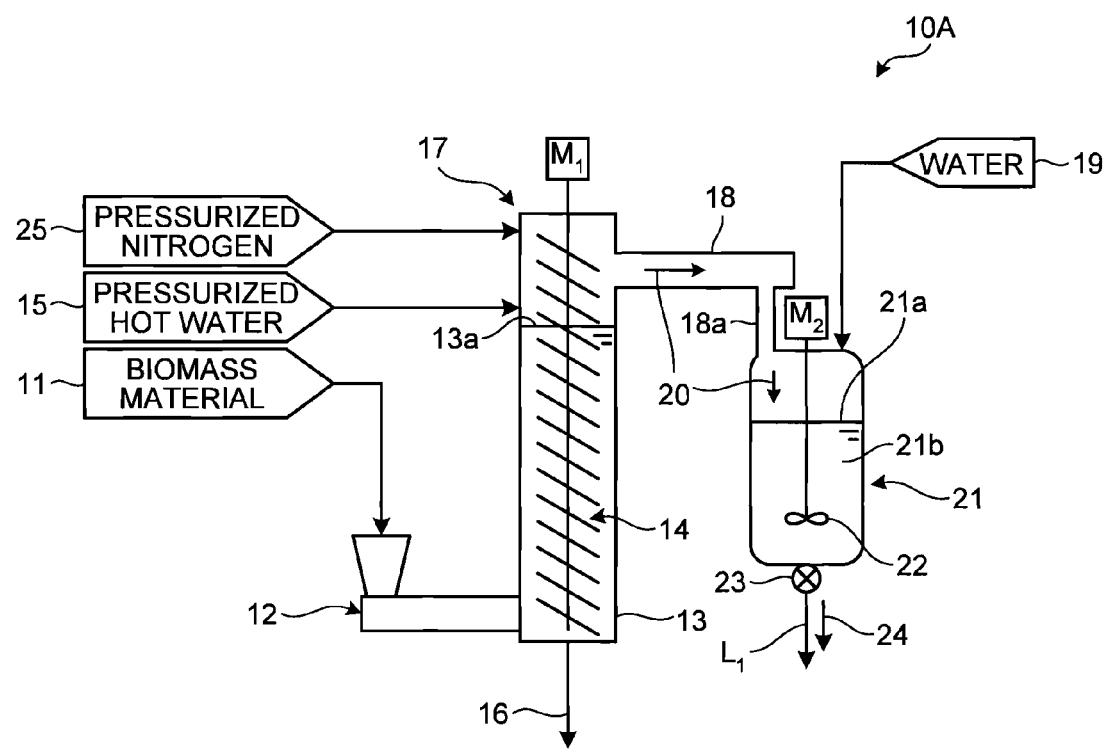
FIG. 1 is a schematic diagram of a biomass processing system according to a first embodiment.

FIG. 1 is a schematic diagram of a biomass processing system according to a first embodiment.

As shown in FIG. 1, a biomass processing system 10A according to the present embodiment includes: a hydrothermal decomposition processing unit 17 as a biomass processing unit that decomposes a biomass material 11 into cellulose, hemicellulose, and lignin under a high temperature and high pressure condition to remove a lignin component and a hemicellulose component in an apparatus body 13, which is a processing vessel having a gas-liquid interface 13a; a biomass solid discharging unit 18 that discharges a biomass solid (a hot-water insoluble component) 20 processed in the hydrothermal decomposition processing unit 17; a slurrying vessel 21 communicating with the biomass solid discharging unit 18, into which water 19 is injected and the discharged biomass solid 20 is added to obtain a slurried biomass solid 24; and a discharge unit 23 that discharges the slurried biomass solid 24 under an increased pressure to put it under a normal pressure.

The hydrothermal decomposition processing unit 17 includes a biomass feeding unit 12 that feeds the biomass material 11 containing cellulose, hemicellulose, and lignin under a normal pressure to put it under an increased pressure.

In the hydrothermal decomposition processing unit 17, the fed biomass material 11 is transported from a lower side to an upper side in the apparatus body 13 by first screw means 14 which is transportation means; pressurized hot water (hereinafter, referred to also as "hot water") 15 is fed from an upper side different from the feed position of the biomass material 11 into the apparatus body 13; hydrothermal decomposition is performed while bringing the biomass material 11 into countercurrent contact with the pressurized hot water 15; and hot-water soluble components (a lignin component and a hemicellulose component) are transferred into a hot-water effluent 16, which is pressurized hot water to be discharged, thereby separating the lignin component and the hemicellulose component from the biomass material 11.

Herein, screw means is exemplified as the transportation means in the present embodiment. However, the transportation means is not limited to the screw means as long as it is capable of transporting the biomass solid from the lower side to the upper side.

The water 19 to be added to the slurrying vessel 21 is only required to be in a liquid state under a pressure in the system in order to achieve liquid seal for the purpose of preventing the leakage of pressurized nitrogen 25 for pressurization. In order to suppress the excessive decomposition (the decomposition starting temperature is about 140° C. to 180° C.) of hemicellulose in water contained in the biomass solid, the temperature of the biomass solid 20 and the temperature of the water 19 to be injected in accordance with the capacity of the slurrying vessel 21 may be suitably set so as to decrease the liquid temperature in the slurrying vessel 21 to 140° C. or less. As the water 19, water typically used within the range of 0° C. to 60° C., for example, (for example, cooling tower water or chiller water), or the like, can be used. As will be described later, water in the system can be circulated for reuse.

In FIG. 1, reference numeral 18a denotes a passage communicating with the biomass solid discharging unit 18 and the slurrying vessel 21, reference numeral 22 denotes stirring means for stirring the inside of the slurrying vessel 21, reference numeral 13a denotes the gas-liquid interface of the hydrothermal decomposition apparatus 13, reference numeral 21a denotes the gas-liquid interface of the slurrying vessel 21, reference letter $L_1$ denotes a discharge line, reference letter $M_1$ denotes a motor for driving the first screw means 14, and reference letter $M_2$ denotes a motor for driving the stirring means 22.

As shown in FIG. 10, the biomass (cellulose material) material 10 contains, in addition to cellulose, hemicellulose and lignin. Specifically, the biomass material 11 has a structure such that cellulose is bundled by hemicellulose with lignin bonding thereto.

After the hydrothermal decomposition, biomass is separated into a hot-water insoluble component (solid) and a hot-water soluble component. The hot-water insoluble component is mainly cellulose (the material of C6 saccharide), and the hot-water soluble component is mainly hemicellulose (the material of C5 saccharide). These are respectively saccharified by enzymes so as to obtain saccharide.

Thus, the biomass material 11 is hydrothermally decomposed by the pressurized hot water 15 in a high temperature (180 to 240° C.) range, and hemicellulose is dissolved on a hot water and lignin is also decomposed and dissolved on the hot water side. As a result, hemicellulose and the like are dissolved on the hot water side.

Hot-water dissolved hemicellulose obtained after being dissolved in hot water causes excessive decomposition in the high temperature (180 to 240° C.) range.

Since the excessive decomposition of hemicellulose causes a reduction in the yield of hemicellulose to be the material of C5 saccharide, it is necessary to suppress the excessive decomposition of hot-water dissolved hemicellulose.

Moreover, the mixing of the excessive decomposition product in hot water becomes a reaction inhibiting factor in a saccharification process by enzymes and a fermentation process such as alcohol fermentation in facilities on a downstream side. Therefore, it is also required to suppress the generation of this inhibitor.

In FIG. 1, the biomass solid discharging unit 18 is provided with second screw means, which is not shown in the figure, and the second screw means discharges the biomass solid 20, which is a hot-water insoluble component and transported from the lower side to the upper side by the first screw means 14, to the slurrying vessel 21 side. Then, the discharged biomass solid 20 is successively dropped in the liquid 21b from the passage 18a and stirred by the stirring means 22 provided in the slurrying vessel 21 so as to be slurried.

The biomass solid 20 dropped in the liquid 21b inside the slurrying vessel 21 is cooled by the direct heat exchange with the liquid 21b, thereby suppressing the excessive decomposition of residual hemicellulose, residual lignin, and the main component, cellulose, due to the hot water accompanying the biomass solid 20.

In a gas atmosphere on the upper side of the gas-liquid interface 13a of the hydrothermal decomposition processing unit 17, the biomass solid 20 is exposed above the hot-water liquid level (gas-liquid interface 13a) by the first screw means 14. However, due to the presence of the pressurized hot water 15 accompanying the biomass solid 20, the reaction is still in progress under the high temperature and high pressure state. Therefore, by adding the biomass solid 20 into the liquid 21b in the slurrying vessel 21, the reaction can be terminated.

Therefore, such a reaction termination leads to the suppression of the excessive decomposition of residual hemicellulose, residual lignin, and the main component, cellulose. As a result, the recovery rate of cellulose is improved since the excessive decomposition of the cellulose component is suppressed, and the generation of the reaction inhibiting component is suppressed on a downstream side.

By injecting the water 19 into the slurrying vessel 21, the liquid 21b is present therein. Therefore, liquid seal is made in the gas-liquid interface 13a of the hydrothermal decomposition processing unit 17 and in the gas-liquid interface 21a of the slurrying vessel 21, thereby preventing the leakage of the pressurized nitrogen 25 which is a pressurizing gas. As a result, loss caused by the gas leakage is eliminated, and it is therefore possible to achieve a substantial reduction in the running cost of the pressurizing gas. Note that the slurrying vessel 21 is provided with a safety valve and an input passage of the pressurized nitrogen 25 which are not shown in the figure.

By slurrying the biomass solid 20, fluidization is obtained and the discharge means for discharging the biomass solid 20 from the slurrying vessel 21 to the outside can be simplified. That is, if the biomass solid 20 is kept in a high temperature state, it is necessary to use an expensive material, for example, as the material for the discharge means. However, since the biomass solid 20 is cooled in the slurrying vessel 21, an inexpensive stainless steel, plastic, or the like, can be employed as the material for the discharge unit 23 provided on the discharge side. As the discharge unit 23, a rotary feeder, a flow control valve, or the like, can be used, for example.

Since the biomass solid 20 has a large porosity and a small bulk density, the handling thereof in a solid state is troublesome. However, by slurrying the biomass solid, a reduction in volume is achieved, and the handling thereof therefore becomes easier.

That is, before added to the liquid 21b, the biomass solid 20 is in the form of a cake, has a large porosity due to its large percentage of the pressurizing gas, and has a small bulk density which is 0.5 g/cc or less. By slurrying the biomass solid 20, the void space is reduced and the slurry becomes dense, thereby achieving a reduction in volume.

Further, by slurrying the biomass solid 20, fluidization is obtained, and the handling thereof in processes thereafter therefore becomes easier.

Particularly, in a saccharification process or the like, since it is an enzyme reaction, the biomass solid needs to be cooled to a predetermined temperature or less (for example, 60° C. or less). In this case, cooling of the biomass solid 20 as it is requires large heat exchange means since the heat exchange efficiency of the solid 20 is not favorable. However, by slurrying the biomass solid 20, favorable cooling efficiency is obtained, thereby eliminating the need for the large heat exchange means.

Indirect cooling means for cooling the inside of the slurrying vessel 21 may be provided.

Although the slurrying vessel 21 is provided with the stirring means 22, the present invention is not limited thereto. For example, the stirring may be performed by circulation means by a pump, or the like.

The biomass to be fed to the hydrothermal decomposition processing unit 17 is not particularly limited, and is defined as organisms incorporated in a substance circulatory system of the global biosphere or accumulation of organic matters derived from the organisms (see JIS K 3600 1258). In the present invention, it is particularly preferable to use cellulose resources such as woods, for example, hardwood, and herbaceous biomass, agricultural waste, food waste, or the like.

The particle diameter of the biomass material 11 is not particularly limited. However, it is preferred to mill the biomass material 11 into those with a size of 5 millimeters or less.

In the present embodiment, before feeding the biomass, for example, a mill may be used as a pre-processing device to perform pre-processing. Further, biomass can be cleaned by a cleaning device.

For example, when hull or the like is used as the biomass material 11, it can be fed as it is to the biomass feeding unit 12 without milling.

It is preferred that the reaction temperature in the hydrothermal decomposition processing unit 17 be in a range from 180 to 240° C., and more preferably from 200 to 230° C.

This is because hydrothermal decomposition rate is low at a low temperature of less than 180° C., and a long decomposing time is required. This leads to an increase in size of the apparatus, and it is not preferable. On the other hand, at a temperature exceeding 240° C., the decomposition rate becomes excessive, transfer of the cellulose component from a solid phase to a liquid phase increases, and excessive decomposition of hemicellulose saccharides is promoted, which is not preferable.

The hemicellulose component dissolves at about 140° C., cellulose dissolves at about 230° C., and the lignin component dissolves at about 140° C. However, it is preferred that cellulose be left on the solid phase, and the temperature be set to a range from 180° C. to 240° C., at which the hemicellulose component and the lignin component can maintain a sufficient decomposition rate.

As a reaction pressure, it is preferred that a pressure higher by 0.1 to 0.5 MPa be applied to a saturated vapor pressure of water at respective temperatures of the reaction temperature (180 to 240° C.) of the apparatus body 13.

It is also preferred that a reaction time be equal to or shorter than 20 minutes, and preferably, from 3 to 10 minutes. This is because if the reaction time is too long, the rate of excessive decomposition product increases, which is not preferable.

As the biomass feeding unit 12 that feeds biomass under a normal pressure to under an increased pressure, for example, means such as a screw, piston pump, or slurry pump can be mentioned.

In the present embodiment, the hydrothermal decomposition apparatus is a vertical apparatus. However, the present invention is not limited thereto, and a gradient-type hydrothermal decomposition apparatus having the gas-liquid interface 13a can be used.

The reason why the hydrothermal decomposition apparatus is the gradient type or vertical type is that gas generated in the hydrothermal decomposition reaction, gas brought into the material, and the like, can quickly escape from above, which is preferable. Further, because the decomposition product is extracted by the pressurized hot water 15, the concentration of the extracted product increases from the upper side toward the lower side, which is preferable in view of the extraction efficiency.

As described above, according to the present embodiment, after the biomass material is decomposed into a cellulose-based component and a hemicellulose component under a solid-liquid contact state, the biomass solid, which is the decomposition product, is added into the liquid injected in the slurrying vessel so as to obtain the slurried biomass solid. The liquid seal is also achieved, so that it is possible to prevent the effluence of the pressurized gas. Thus, the effluence of pressurizing gas (for example, pressurized nitrogen or the like) is prevented, thereby achieving a substantial reduction in the running cost.

In the present embodiment, a description has been made while using the hydrothermal decomposition apparatus as the biomass processing unit that decomposes biomass. However, the present invention is not limited thereto. For example, even an alkaline decomposition biomass processing unit (for example, decomposition by using sodium hydroxide, calcium hydroxide, or ammonia, or the like) or an acid decomposition biomass processing unit (decomposition by diluted sulfuric acid, or the like) can be applied to a system in which a gas-liquid interface is provided, and when discharging, in a solid state, the biomass solid 20 after the process from the biomass processing unit, the slurrying vessel 21 is provided for slurrying the processed biomass solid and the slurried biomass solid is discharged through a discharge means from under an increased pressure to under a normal pressure.

Second Embodiment

A biomass processing system according to another embodiment of the present invention will next be described with reference to the drawing. Elements identical to those in the biomass processing system according to the first embodiment are denoted by like reference letters or numerals and explanations thereof will be omitted.

Figure 2:
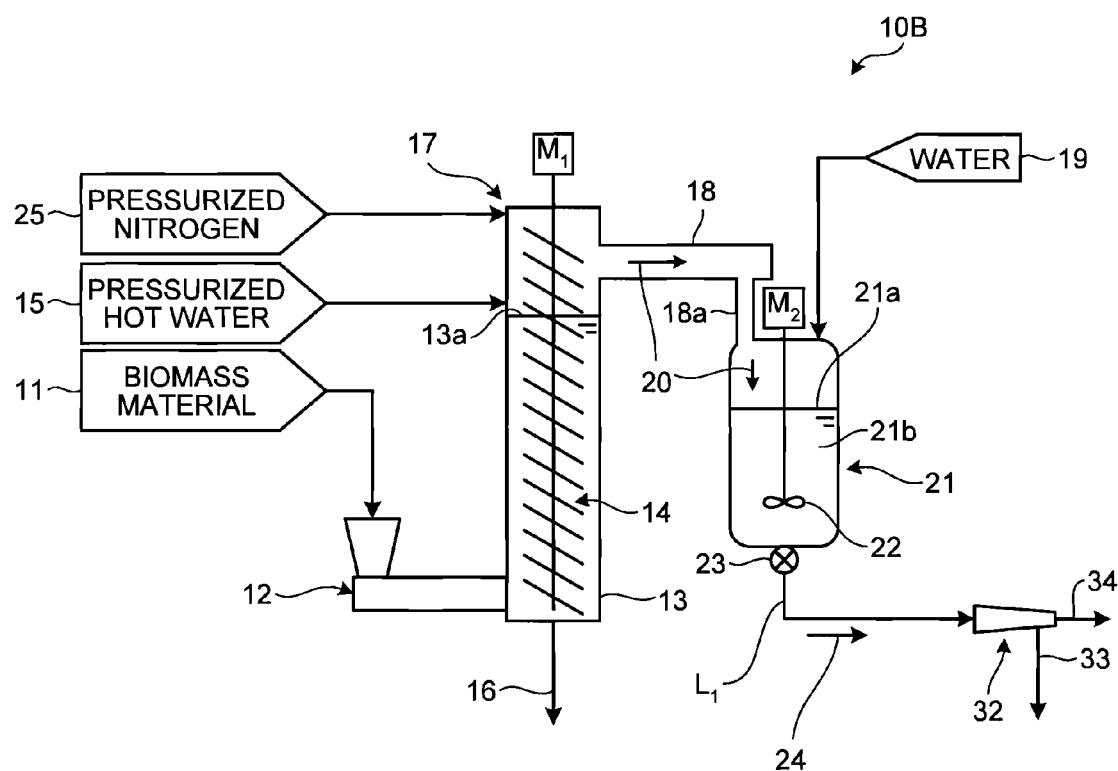
FIG. 2 is a schematic diagram of a biomass processing system according to a second embodiment.

FIG. 2 is a schematic diagram of a biomass processing system according to a second embodiment.

As shown in FIG. 2, a biomass processing system 10B further includes, in the biomass processing system 10A according to the first embodiment, a first solid-liquid separation device 32 provided in the discharge line $L_1$ of the slurried biomass solid 24 discharged from the slurrying vessel 21. The first solid-liquid separation device 32 removes water 34 containing a reaction inhibiting substance to obtain a biomass solid 33. By removing the water 34 by the first solid-liquid separation device 32, a desired solid concentration can be obtained. Thus, it becomes possible to adjust a substrate concentration in the saccharification reaction on the downstream side.

That is, according to the present embodiment, since the water 34 containing a reaction inhibiting substance is separated from the biomass solid 33 in the first solid-liquid separation device 32, the reaction inhibiting substance can be efficiently removed, thereby obtaining a favorable reaction on the downstream side.

Third Embodiment

A biomass processing system according to another embodiment of the present invention will be described with reference to the drawing. Elements identical to those in the biomass processing systems according to the first and second embodiments are denoted by like reference letters or numerals and explanations thereof will be omitted.

Figure 3:
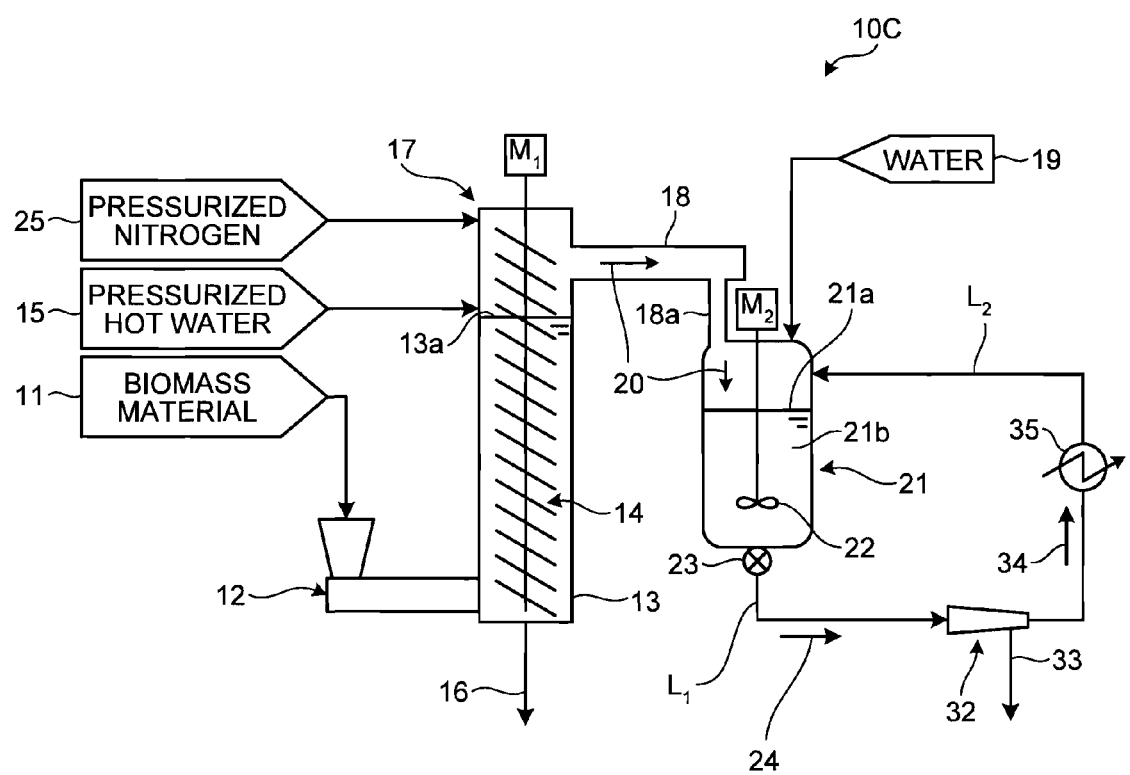
FIG. 3 is a schematic diagram of a biomass processing system according to a third embodiment.

FIG. 3 is a schematic diagram of a biomass processing system according to a third embodiment.

As shown in FIG. 3, a biomass processing system 10C includes, in the biomass processing system 10B according to the second embodiment, a first return line $L_2$ for recycling, to the slurrying vessel 21, the water 34 separated by the first solid-liquid separation device 32.

Further, a cooler 35 is provided in the first return line $L_2$ to cool the water to a predetermined temperature, and the cooled water is then returned to the slurrying vessel 21.

Accordingly, the separated water 34 can be reused, thereby reducing the amount of use of the water 19 separately fed to the slurrying vessel 21.

Fourth Embodiment

A biomass processing system according to another embodiment of the present invention will be described with reference to the drawing. Elements identical to those in the biomass processing systems according to the first to third embodiments are denoted by like reference letters or numerals and explanations thereof will be omitted.

Figure 4:
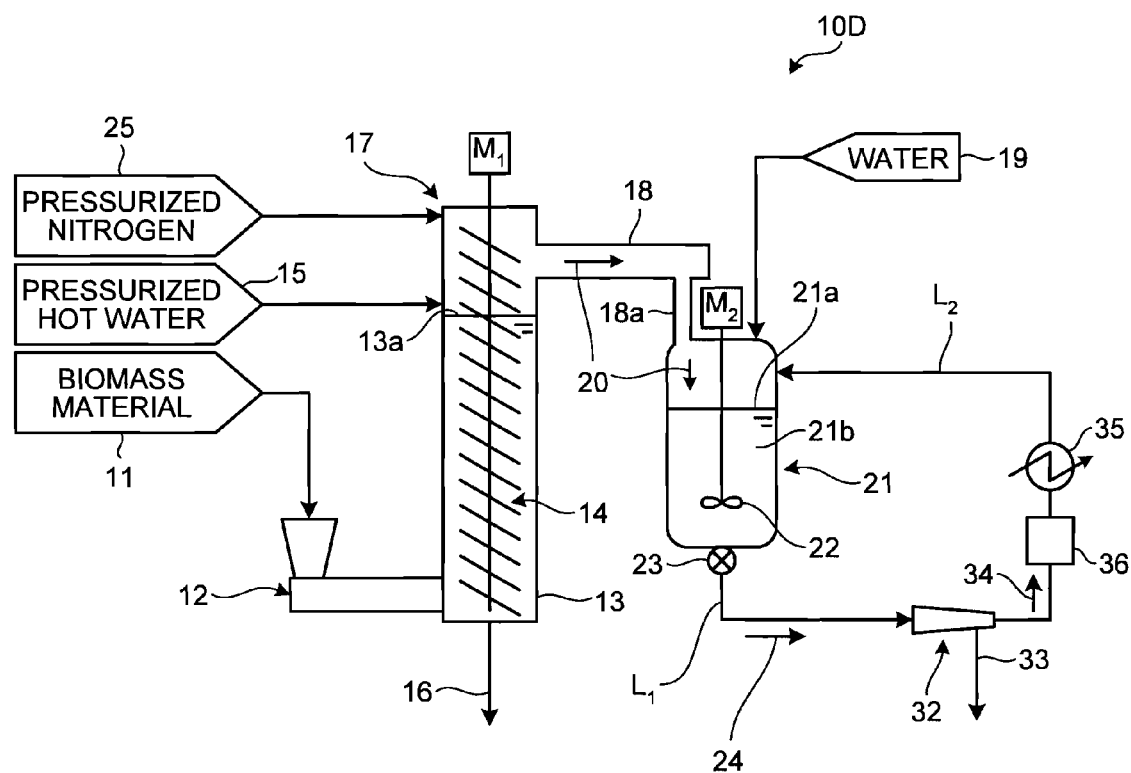
FIG. 4 is a schematic diagram of a biomass processing system according to a fourth embodiment.

FIG. 4 is a schematic diagram of a biomass processing system according to a fourth embodiment.

As shown in FIG. 4, a biomass processing system 10D further includes, in the biomass processing system 10C according to the third embodiment, a biological treatment vessel 36 for performing biological treatment on the water 34 separated by the first solid-liquid separation device 32 in the first return line $L_2$. After cooling the biologically-treated water 34 by the cooler 35, the water is returned to the slurrying vessel 21.

Since the separated water 34 includes organic acid (for example, formic acid, acetic acid, citric acid, or the like) which is a reaction inhibiting substance on the downstream side, such an organic acid is decomposed and removed by the biological treatment vessel 36. Such a process is reliably performed, and therefore an inhibiting substance has been removed upon the reuse as the water 19. Thus, upon the reaction termination in the slurrying vessel 21, there is no increase in the inhibiting substance.

Further, by using, for example, a methane fermentation biological treatment device as a biological treatment device 61, methane is recovered and can be used as a fuel or the like.

Fifth Embodiment

A biomass processing system according to another embodiment of the present invention will be described with reference to the drawing. Elements identical to those in the biomass processing systems according to the first to fourth embodiments are denoted by like reference letters or numerals and explanations thereof will be omitted.

Figure 5:
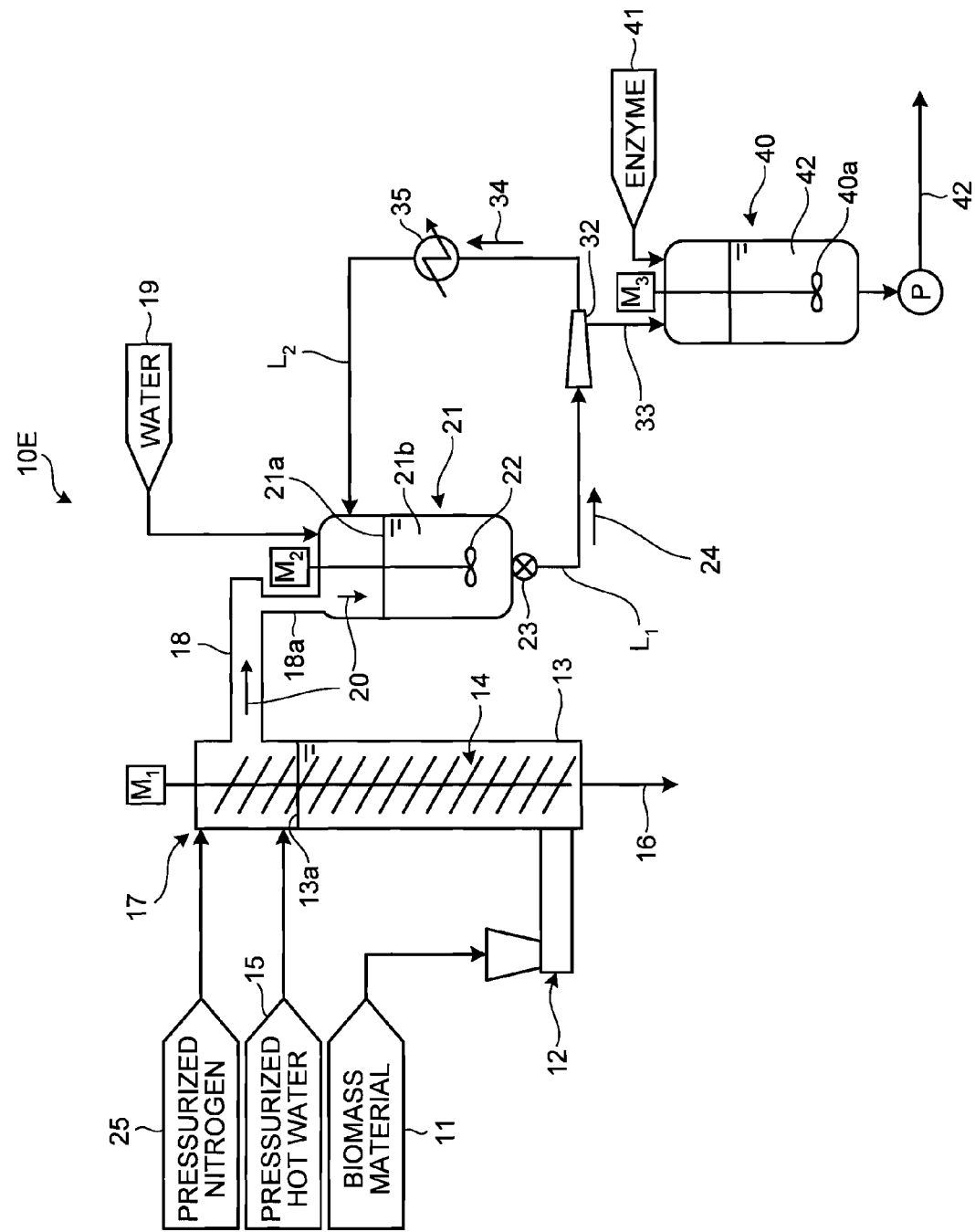
FIG. 5 is a schematic diagram of a biomass processing system according to a fifth embodiment.

FIG. 5 is a schematic diagram of a biomass processing system according to a fifth embodiment.

As shown in FIG. 5, a biomass processing system 10E includes, in the biomass processing system 10C according to the third embodiment, a first saccharification tank 40 for saccharifying the biomass solid 33 separated by the first solid-liquid separation device 32 by using an enzyme 41 so that the biomass solid 33 is saccharified to obtain a saccharide solution (C6 saccharide) 42. In FIG. 5, reference numeral 40a denotes stirring means, and reference letter $M_3$ denotes a motor for driving the stirring means 40a.

In the present embodiment, since the unnecessary water 34 is removed by the first solid-liquid separation device 32 to condense the biomass solid 33 to a desired concentration, it is possible to perform saccharification at a higher substrate concentration, thereby increasing the concentration of C6 saccharide. Moreover, while the water came along from the hydrothermal decomposition processing unit 17 and contained in the solid contains a substance that inhibits fermentation, and the like, since the water 34 is removed by the first solid-liquid separation device 32, saccharification can be performed with such substances being removed. As a result, the quality of the saccharide is improved.

Further, through the first solid-liquid separation device 32, it becomes possible to adjust a substrate concentration to any desired concentration. For example, in order to increase a saccharide concentration after saccharification, the water removal rate in the first solid-liquid separation device 32 may be increased to perform saccharification at a higher substrate concentration as described above. In order to perform saccharification or stirring and transportation after saccharification with an improved operability, or in order to increase the saccharification speed, the water removal rate may be lowered to perform saccharification at a lower substrate concentration.

Sixth Embodiment

A biomass processing system according to another embodiment of the present invention will be described with reference to the drawing. Elements identical to those in the biomass processing system according to the fifth embodiment are denoted by like reference letters or numerals and explanations thereof will be omitted.

Figure 6:
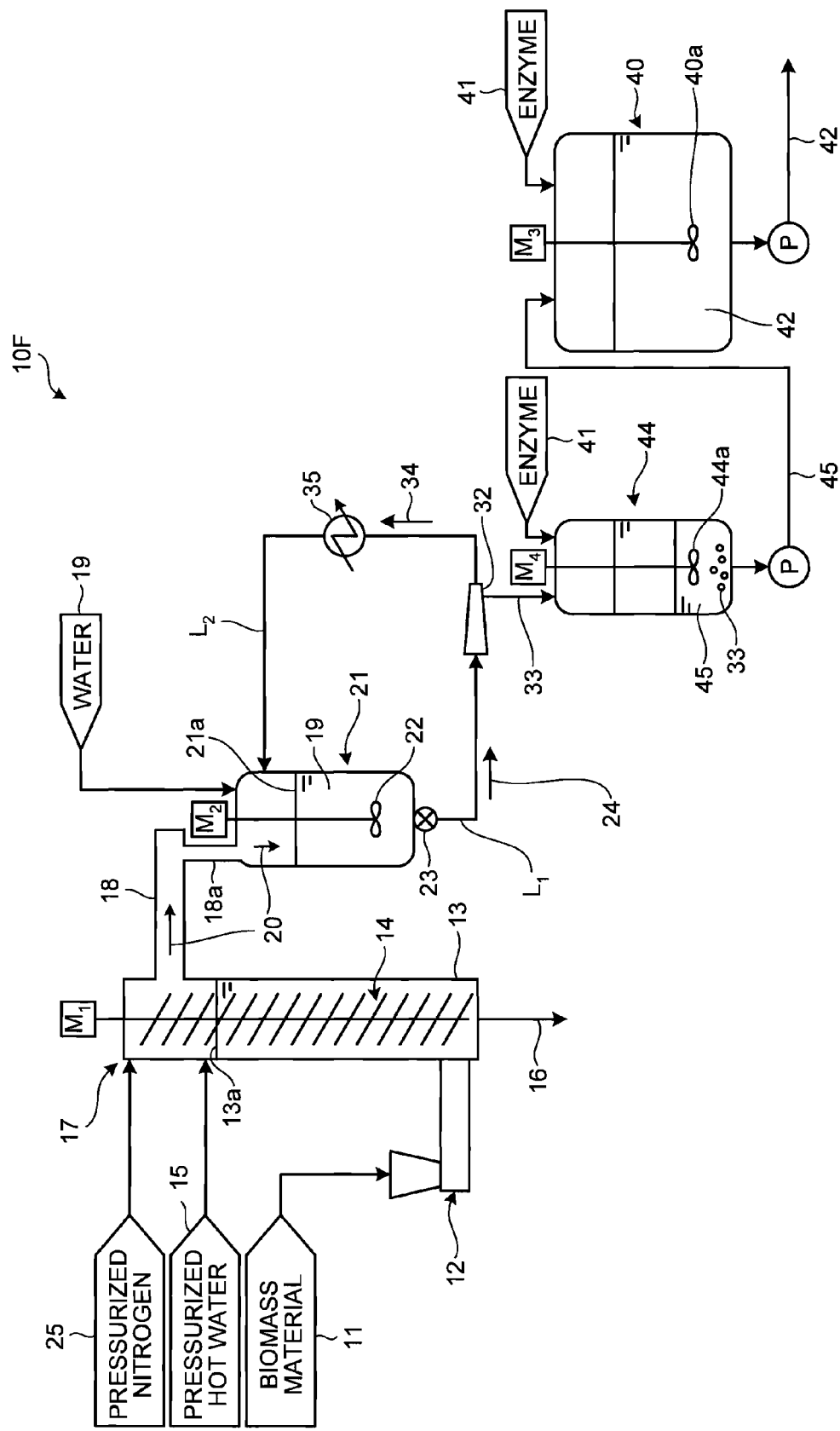
FIG. 6 is a schematic diagram of a biomass processing system according to a sixth embodiment.

FIG. 6 is a schematic diagram of a biomass processing system according to a sixth embodiment.

As shown in FIG. 6, a biomass processing system 10F includes, in the biomass processing system 10E according to the fifth embodiment, an enzyme liquefaction tank 44 for performing enzyme liquefaction by adding the enzyme 41 to the biomass solid 33 separated by the first solid-liquid separation device 32.

In the enzyme liquefaction tank 44, liquefaction is made by hydrolysis of the biomass solid 33 using the enzyme 41 such as cellulase, for example, to produce oligosaccharide, for example. Then, the oligosaccharide, which is an enzyme liquefied product 45, is further hydrolyzed to perform saccharification (monosaccharification: mainly the production of C6 saccharide).

In the present embodiment, a biomass material is fed for a hydrothermal decomposition process so as to continuously obtain the biomass solid 24. Thereafter, the biomass solid is slurried in the slurrying vessel 21, the biomass solid 33 is then separated therefrom by the first solid-liquid separation device 32, and the enzyme 41 is added thereto to obtain the enzyme liquefied product 45 in the enzyme liquefaction tank 44. Thereafter, the enzyme liquefied product 45 is introduced into the separately-provided large first saccharification tank 40 to perform batch saccharification for a predetermined reaction time so as to obtain the saccharide solution (C6 saccharide) 42. If the large first saccharification tank 40 is filled up with the liquefied product 45, another large first saccharification tank 40 which is not shown in the drawings may be used to perform the batch process.

Although the amount of the enzyme 41 to be added into the enzyme liquefaction tank 44 is only necessary to be the amount needed to liquefy the biomass solid in the enzyme liquefaction tank 44 with a good operability, the amount of enzyme capable of sufficiently performing saccharification in the first saccharification tank 40 on the downstream may be added to the enzyme liquefaction tank 44, for example. Alternatively, placing a great value only on its operability, the amount of the enzyme 41 just enough to perform liquefaction may be added in the enzyme liquefaction tank 44, and the amount of the enzyme 41 just enough to perform sufficient saccharification may be added in the first saccharification tank 40 on the downstream side.

In the drawing, reference numeral 44a denotes stirring means, and reference letter $M_4$ denotes a motor for driving the stirring means 44a.

In the present embodiment, since the biomass solid 33 is once liquefied in the enzyme liquefaction tank 44, transportation by a pump, for example, becomes possible, thereby improving the handling ability. Moreover, since liquefaction facilitates stirring, the stirring power of the stirring means $M_3$ of the first saccharification tank 40 can be made small. Further, since enzyme reaction occurs in liquid, the reaction speed is accelerated, thereby contributing to reductions in size and power of the large first saccharification tank 40A and achieving a reduction in the amount of enzyme used.

In the present embodiment, it is preferred that the separated biomass solid 33 be continuously and gradually added to the enzyme liquefied product 45 obtained in the enzyme liquefaction tank 40. That is, the biomass solid 33 separated by the first solid-liquid separation device 32 is continuously and gradually added into the enzyme liquefied product which has been liquefied in the enzyme liquefaction tank 40 so as to make an adjustment such that the biomass solid, which has a low fluidity, does not exist in the enzyme liquefaction tank 40 as far as possible. Accordingly, stirring capability in the enzyme liquefaction tank 40 and transferability to the enzymatic saccharification tank on a downstream are improved, thereby allowing for a facility operation with a good operability.

In contrast, if the enzyme liquefaction operation is performed when the biomass solid exists in a large amount in the enzyme liquefaction tank 40, i.e., when the enzyme 41 is added to a large amount of the biomass solid 33 to make liquefaction gradually progress starting from a portion thereof, it will induce a reduction in the production capability and a reduction in the operability in continuous operation.

As described above, according to the present invention, the process up to the enzymatic saccharification tank 44 after continuously adding the biomass material 11 to the hydrothermal decomposition processing unit 17 can be processed continuously. Thus, it is only necessary to design the capacity or the number of the first saccharification tank 40 for performing sufficient saccharification in accordance with the production capability of the enzyme liquefaction on the upstream side, thereby allowing for a substantial improvement in the facility efficiency and workability thereof.

As described above, as shown in FIG. 5, for example, a saccharide-solution production method using a biomass material according to the present invention includes: feeding a biomass material 11 containing cellulose, hemicellulose, and lignin under a normal pressure to put it under an increased pressure; hydrothermally decomposing the biomass material 11 using pressurized hot water 15 by a hydrothermal decomposition processing unit 17; dissolving a lignin component and a hemicellulose component in the pressurized hot water 15; thereafter, adding a biomass solid 20 discharged from the hydrothermal decomposition processing unit 17 to a slurrying vessel 21 containing water 19 injected therein and communicating with the hydrothermal decomposition processing unit 17 so as to obtain a slurried biomass solid 24; then removing water 34 from the slurried biomass solid 24 by a first solid-liquid separation device 32; and thereafter, performing enzymatic saccharification of a biomass solid 33 from which water has been removed, thereby making it possible to efficiently produce a saccharide solution 42.

In the above-described saccharide-solution production method using a biomass material, as shown in FIG. 6, for example, enzyme liquefaction is first performed on the upstream of enzymatic saccharification and enzymatic saccharification is then performed by using the enzyme liquefied product 45, thereby improving the productivity of the saccharide solution 42.

Seventh Embodiment

A biomass processing system according to another embodiment of the present invention will be described with reference to the drawing. Elements identical to those in the biomass processing system according to the first embodiment are denoted by like reference letters or numerals and explanations thereof will be omitted.

Figure 7:
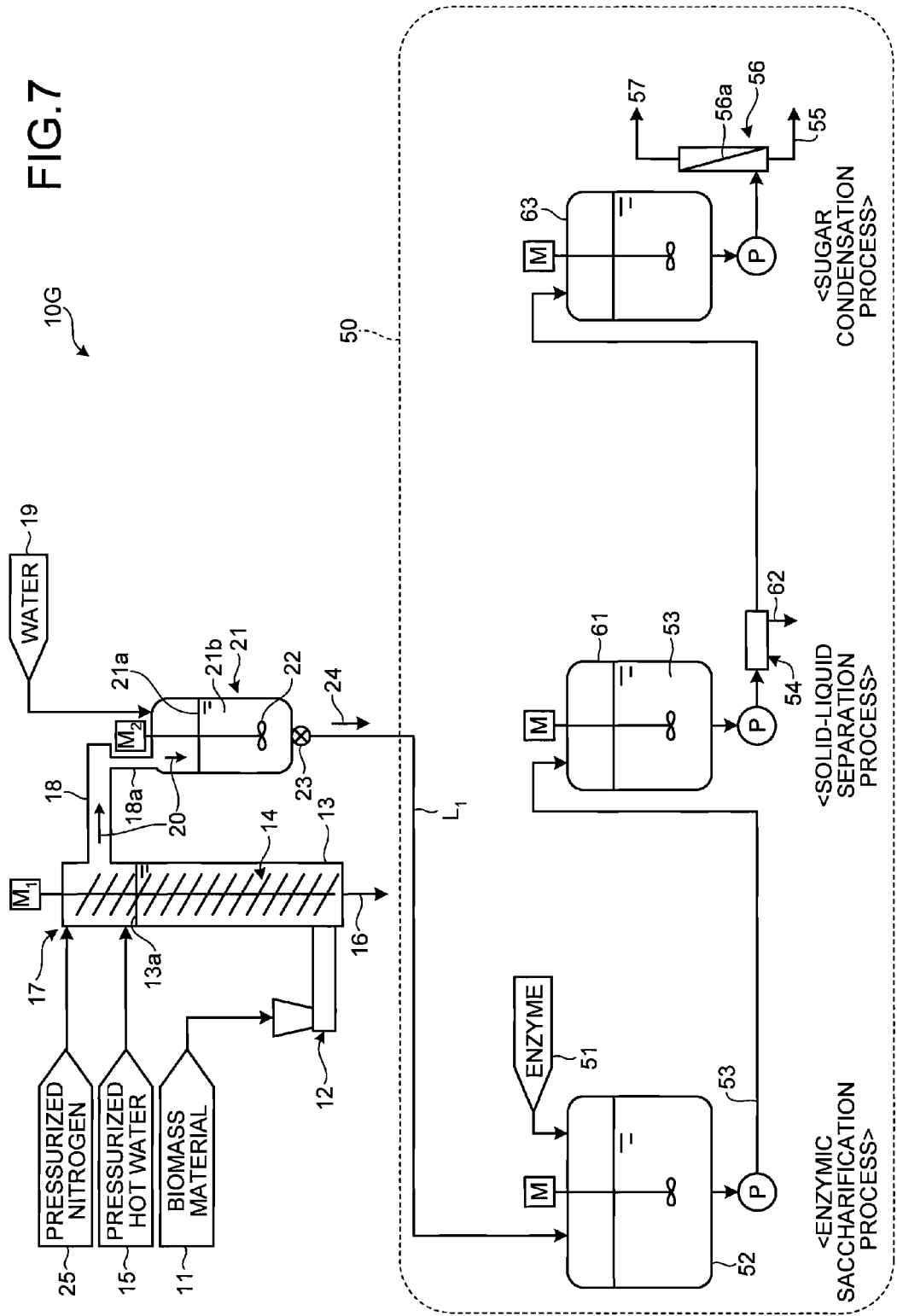
FIG. 7 is a schematic diagram of a biomass processing system according to a seventh embodiment.

FIG. 7 is a schematic diagram of a biomass processing system according to a seventh embodiment.

As shown in FIG. 7, a biomass processing system 10G includes, in the biomass processing system 10A according to the first embodiment, a C6 saccharification and saccharide condensation device 50 that performs enzymatic saccharification of a biomass solid mainly containing a cellulose component to obtain hexose (C6 saccharide) or the like and condenses the saccharide.

The C6 saccharification and saccharide condensation device 50 includes: a second saccharification tank 52 for performing enzymatic saccharification of the slurried biomass solid 24 by an enzyme 51; a second solid-liquid separation device 54 that separates a solid content from a saccharide solution 53 after the saccharification; and a water separation device 56 having a reverse osmosis (RO) membrane 56a that removes water 57 from the saccharide solution 53 separated by the second solid-liquid separation device 54 to obtain a condensed saccharide solution 55.

For example, the second solid-liquid separation device 54 may use a screw decanter, a sand filtration device, an MF membrane, or the like, solely or in a combination thereof. As a result, the solid is removed, and the protection of the RO membrane 56a is therefore achieved. Further, on the preceding stage of the RO membrane 56a, an ultrafiltration membrane (UF membrane) can be used to protect the RO membrane and enable the recovery of the enzyme, thereby allowing for reuse of the enzyme.

The water separation device 56 may employ a loose RO membrane, a nanofiltration membrane (NF membrane), or the like.

A procedure of the processes of the C6 saccharification and saccharide condensation device 50 will be described.

<Enzymatic Saccharification Process>

First, the slurried biomass solid 24 is introduced in the above-described saccharification tank 52 through the discharge line $L_1$ and the enzyme 51 is added thereto so as to perform saccharification due to enzyme reaction in the enzymatic saccharification process.

<Solid-Liquid Separation Process>

Next, the saccharide solution 53 is stored in a first saccharide-solution tank 61, solid residual liquid 62 such as lignin is then separated by the second solid-liquid separation device 54, and the saccharide solution 53 is then stored in a second saccharide solution tank 63.

<Saccharide Condensation Process>

Next, the water 57 is removed from the saccharide solution 53 by the water separation device 56 including the RO membrane 56a to obtain the condensed saccharide solution 55.

The condensed saccharide solution 55 is turned into various organic materials in a fermentation process which is a subsequent process not shown in the figure.

In the present embodiment, since the slurried biomass solid 24 is used to perform saccharification, saccharification is made at a low substrate concentration, thereby allowing for high-speed saccharification.

Further, such a slurried state enables stirring and transportation, etc., to be performed with a good operability.

Further, since saccharification is made at a low substrate concentration, it is possible to reduce the amount of enzyme used.

Further, the membrane processes using various membranes make it possible to efficiently perform saccharide condensation.

Further, since the separated solid residual liquid such as lignin has a high calorie, it can be used as a fuel. Further, the solid residual liquid 62 such as lignin can be employed for an organic fertilizer application or a chemical raw material application (for example, an application as a lignin adhesive).

As described above, as shown in FIG. 7, a saccharide-solution production method using a biomass material according to the present invention includes: feeding a biomass material 11 containing cellulose, hemicellulose, and lignin under a normal pressure to put it under an increased pressure; hydrothermally decomposing the biomass material 11 using pressurized hot water 15 by a hydrothermal decomposition processing unit 17; dissolving a lignin component and a hemicellulose component in the pressurized hot water 15; thereafter, adding a biomass solid 20 discharged from the hydrothermal decomposition processing unit 17 to a slurrying vessel 21 containing water 19 injected therein and communicating with the hydrothermal decomposition processing unit 17 so as to obtain a slurried biomass solid 24; performing enzymatic saccharification of the slurried biomass solid 24 to obtain a saccharide solution 53; thereafter, separating a solid content therefrom; and then removing water therefrom. Thus, it is possible to efficiently produce a saccharide solution from the biomass material.

Eighth Embodiment

A biomass processing system according to another embodiment of the present invention will be described with reference to the drawing. Elements identical to those in the biomass processing system according to the seventh embodiment are denoted by like reference letters or numerals and explanations thereof will be omitted.

Figure 8:
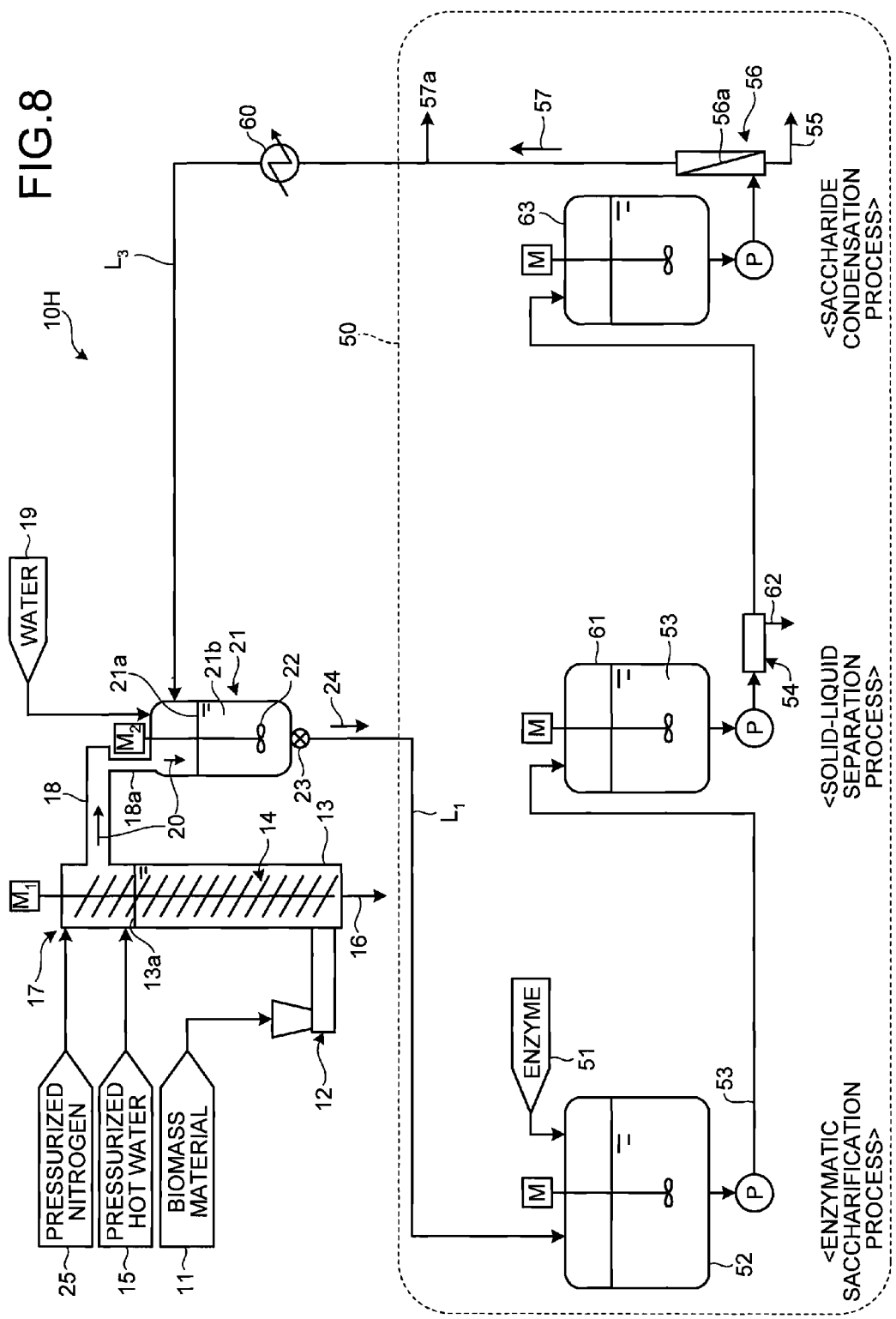
FIG. 8 is a schematic diagram of a biomass processing system according to an eighth embodiment.

FIG. 8 is a schematic diagram of a biomass processing system according to an eighth embodiment.

As shown in FIG. 8, a biomass processing system 10H further includes, in the biomass processing system 10G according to the seventh embodiment, a second return line $L_3$ for recycling the water 57 separated from the water separation device 56 to the slurrying vessel 21.

Further, a cooler 60 is provided in the second return line $L_3$ so as to cool the water to a predetermined temperature, and the cooled water is then returned to the slurrying vessel 21. The cooler 60 may be provided in the discharge line $L_1$ of the slurried biomass solid 24 to perform cooling to a temperature desired in the second saccharification tank 52. In such a case, the cooler 60 in the line $L_3$ can be omitted.

Accordingly, the separated water 57 can be reused, thereby reducing the amount of use of the water 19 separately fed to the slurrying vessel 21.

Ninth Embodiment

A biomass processing system according to another embodiment of the present invention will be described with reference to the drawing. Elements identical to those in the biomass processing system according to the seventh embodiment are denoted by like reference letters or numerals and explanations thereof will be omitted.

Figure 9:
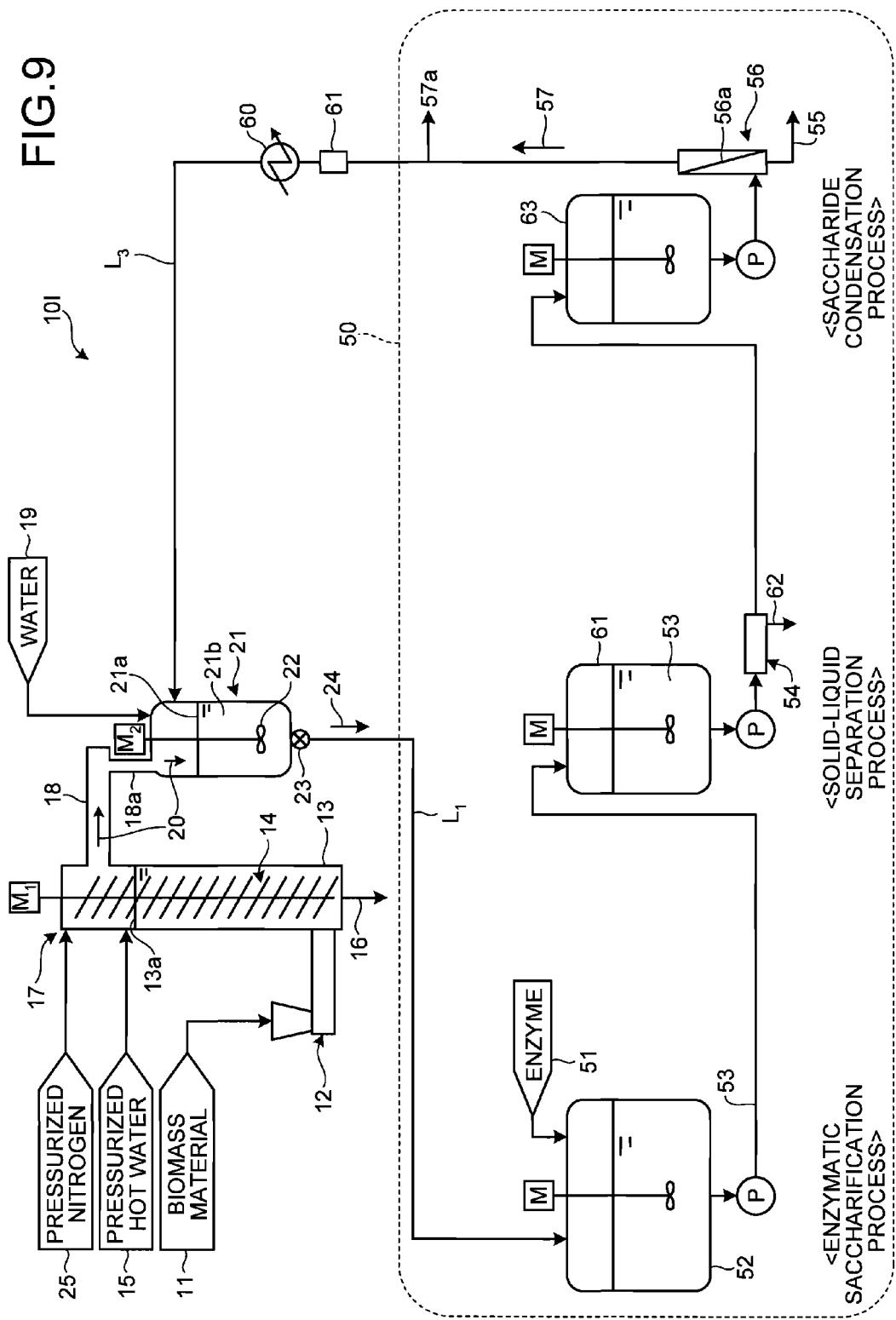
FIG. 9 is a schematic diagram of a biomass processing system according to a ninth embodiment.

FIG. 9 is a schematic diagram of a biomass processing system according to a ninth embodiment.

As shown in FIG. 9, a biomass processing system 10I further includes, in the biomass processing system 10H according to the eighth embodiment, a biological treatment device 61 provided in the second return line $L_3$. After the water 57 is subjected to a biological treatment, the water 57 is returned to the slurrying vessel 21.

Since the water 57 separated by the RO membrane 56a contains a reaction inhibiting substance (low-molecular organic compound), the treatment thereof becomes easier by the biological treatment device 61. By using, for example, a methane fermentation biological treatment device as the biological treatment device, methane is recovered and can be used as a fuel or the like.

As described above, according to the biomass processing system of the present invention, after the biomass material is decomposed into a cellulose-based component and a hemicellulose component under a high temperature and high pressure condition, the biomass solid, which is the decomposition product, is added in the liquid provided inside the slurrying vessel so as to obtain the slurried biomass solid and achieve liquid seal. As a result, it is possible to prevent the effluence of the pressurized gas. Thus, the effluence of the pressurizing gas (for example, pressurized nitrogen or the like) is prevented, thereby reducing the running cost.

By slurrying a biomass solid, the handling thereof becomes easier, which is suitable for the saccharification process thereafter. As a result, it is possible to efficiently produce a saccharide solution (C6 saccharide). Further, it is possible to efficiently produce various organic materials (for example, alcohol, petroleum substitutes, or amino acid) from the saccharide solution. Also, various organic materials (for example, alcohol, petroleum substitutes, or amino acid) such as LPG, automotive fuel, aircraft jet fuel, kerosene petroleum, diesel oil, various heavy oils, fuel gas, naphtha, ethylene glycol as naphtha decomposition product, lactic acid, alcohol (ethanol and the like), amine, alcohol ethoxylate, vinyl chloride polymer, alkyl aluminum, PVA, vinyl acetate emulsion, polystyrene, polyethylene, polypropylene, polycarbonate, MMA resin, nylon, and polyester, for example, can be efficiently produced from the saccharide solution. Therefore, the saccharide solution derived from biomass can be efficiently used as substitutes of chemical products derived from crude oil, which is a depleting fuel, and as a raw material for producing the substitutes.

Further, since the biomass solid is added in the liquid, the reaction can be efficiently terminated by cooling the biomass solid by the direct heat exchange with the liquid. Also, since acid or alkali is diluted, the excessive decomposition of residual hemicellulose, residual lignin, and the main component, cellulose, accompanying the biomass solid is suppressed. As a result, the generation of the reaction inhibiting component can be suppressed, and the recovery rate of the cellulose component can be improved.

INDUSTRIAL APPLICABILITY

As described above, according to the biomass processing system of the present invention, when separating a cellulose-based component from a biomass material, slurrying is performed, thereby allowing for efficient discharge thereof. Further, a saccharide solution is produced by using the slurried product, and various organic materials (for example, alcohol, petroleum substitutes, or amino acid) can be efficiently produced from the saccharide solution.

REFERENCE SIGNS LIST 10A to 10G biomass processing system
11 biomass material
12 biomass feeding unit
13 apparatus body
14 first screw means
15 pressurized hot water
16 hot-water effluent
17 hydrothermal decomposition unit
18 biomass solid discharging unit
19 water
20 biomass solid
21 slurrying vessel
22 stirring means
23 discharge unit
24 slurried biomass solid
25 pressurized nitrogen

The invention claimed is:

1. A biomass processing system comprising:
a decomposition liquid supply unit that supplies a decomposition liquid for decomposing a biomass material;
a pressurizing gas supply unit that supplies a pressurizing gas for pressurizing an inside of the processing vessel;
a biomass processing unit that decomposes a biomass material containing cellulose, hemicellulose, and lignin under a high temperature and high pressure condition by a processing vessel having a first gas-liquid interface to remove a lignin component and a hemicellulose component, so as to obtain a biomass solid, wherein the biomass processing unit comprises:
    a biomass material inlet that is provided at a lower side of the processing vessel and introduces the biomass material into the processing vessel;
    a decomposition liquid inlet that is provided at an upper side of the processing vessel and introduces the decomposition liquid from the decomposition liquid supply unit;
    a pressurizing gas inlet that introduces the pressurizing gas into the processing vessel from the pressurizing gas supply unit; and
    a biomass solid outlet that is provided at an upper side of the processing vessel and from which the decomposed biomass material is discharged as the biomass solid;
a biomass solid discharging unit that is connected to the biomass solid outlet and discharges the biomass solid; and
a slurrying vessel communicating with the biomass solid discharging unit, into which water is injected and the discharged biomass solid is slurried as a slurried biomass, so as to obtain a second gas-liquid interface of the slurried biomass, wherein the slurrying vessel comprises:
    a biomass solid inlet that communicates with the biomass solid discharging unit and that introduces the biomass solid; and
    a slurried biomass outlet from which the slurried biomass is discharged,
wherein the biomass processing unit is configured to provide the first gas-liquid interface between the biomass material inlet and the biomass solid outlet, wherein the slurrying vessel is configured to provide the second gas-liquid interface between the biomass solid inlet and the slurried biomass outlet, and wherein a liquid seal is provided between the first gas-liquid interface and the second gas-liquid interface to prevent leakage of the pressurized gas, wherein the biomass processing system further comprises:

a discharge line that is connected to the slurried biomass outlet to discharge the slurried biomass as a slurried biomass solid;

a solid-liquid separation device that is connected to the discharge line to separate the slurried biomass solid into a biomass solid and water, the water containing a reaction inhibiting substance;

a return line that connects the solid-liquid separation device and the slurrying vessel to return the water to the slurrying vessel;

a biological treatment vessel that is provided in the return line and performs biological treatment on the reaction inhibiting substance contained in the water to decompose and remove the reaction inhibiting substance from the water;

a saccharification tank that is connected to the solid-liquid separation device to perform enzyme liquefaction on the slurried biomass solid by adding an enzyme therein and obtain a saccharide solution.

2. The biomass processing system according to claim 1, wherein the biomass processing unit is any one of a hydrothermal decomposition processing unit, an alkaline decomposition processing unit, and an acid decomposition processing unit.

3. A biomass processing system comprising:

a decomposition liquid supply unit that supplies a decomposition liquid for decomposing a biomass material;

a pressurizing gas supply unit that supplies a pressurizing gas for pressurizing an inside of the processing vessel;

a biomass processing unit that decomposes a biomass material containing cellulose, hemicellulose, and lignin under a high temperature and high pressure condition by a processing vessel having a first gas-liquid interface to remove a lignin component and a hemicellulose component, so as to obtain a biomass solid, wherein the biomass processing unit comprises:

a biomass material inlet that is provided at a lower side of the processing vessel and introduces the biomass material into the processing vessel;

a decomposition liquid inlet that is provided at an upper side of the processing vessel and introduces the decomposition liquid from the decomposition liquid supply unit;

a pressurizing gas inlet that introduces the pressurizing gas into the processing vessel from the pressurizing gas supply unit; and a biomass solid outlet that is provided at an upper side of the processing vessel and from which the decomposed biomass material is discharged as the biomass solid;

a biomass solid discharging unit that is connected to the biomass solid outlet and discharges the biomass solid; and a slurrying vessel communicating with the biomass solid discharging unit, into which water is injected and the discharged biomass solid is slurried as a slurried biomass, so as to obtain a second gas-liquid interface of the slurried biomass, wherein the slurrying vessel comprises:

a biomass solid inlet that communicates with the biomass solid discharging unit and that introduces the biomass solid; and a slurried biomass outlet from which the slurried biomass is discharged, wherein the biomass processing unit is configured to provide the first gas-liquid interface between the biomass material inlet and the biomass solid outlet, wherein the slurrying vessel is configured to provide the second gas-liquid interface between the biomass solid inlet and the slurried biomass outlet, and wherein a liquid seal is provided between the first gas-liquid interface and the second gas-liquid interface to prevent leakage of the pressurized gas, wherein the biomass processing system further comprises:

a discharge line that is connected to the slurried biomass outlet to discharge the slurried biomass as a slurried biomass solid;

a saccharification tank that is connected to the discharge line and performs enzymatic saccharification of the slurried biomass solid by an enzyme to produce a saccharide solution;

a water separation device that is provided downstream of the saccharification tank to separate water from the saccharide solution and obtain a condensed saccharide solution;

a return line that connects the slurrying vessel and the water separation device to return the water from the water separation device to the slurrying vessel;

a biological treatment device that is provided in the return line, and performs a biological treatment on a reaction inhibiting substance contained in the water to decompose and remove the reaction inhibiting substance from the water.

* * * * *